(12) United States Patent
Hashimoto et al.

(10) Patent No.: US 7,300,947 B2
(45) Date of Patent: Nov. 27, 2007

(54) N-DIHYDROXYALKYL-SUBSTITUTED 2-OXO-IMIDAZOLE DERIVATIVES

(75) Inventors: Masaya Hashimoto, Tsukuba (JP); Yoshikazu Iwasawa, Tsukuba (JP); Hiroshi Kawamoto, Tsuchiura (JP); Hisashi Ohta, Tsukuba (JP); Satoshi Ozaki, Tsukuba (JP); Takeshi Sagara, Tsukuba (JP); Hiroki Sakoh, Tsukuba (JP); Atsushi Satoh, Tsukuba (JP)

(73) Assignee: Banyu Pharmaceutical Co., Ltd., Kudankita, Chiyoda-Ku, Tokyo (JP)

( * ) Notice: Subject to any disclaimer, the term of this patent is extended or adjusted under 35 U.S.C. 154(b) by 0 days.

(21) Appl. No.: 11/484,203

(22) Filed: Jul. 11, 2006

(65) Prior Publication Data

US 2007/0015792 A1    Jan. 18, 2007

Related U.S. Application Data

(60) Provisional application No. 60/700,770, filed on Jul. 20, 2005.

(30) Foreign Application Priority Data

Jul. 13, 2005   (JP)   ............................. 2005-204264

(51) Int. Cl.
| | | |
|---|---|---|
| *A01N 43/40* | (2006.01) | |
| *A01N 43/52* | (2006.01) | |
| *A61K 31/445* | (2006.01) | |
| *A61K 31/415* | (2006.01) | |
| *C07D 211/32* | (2006.01) | |
| *C07D 403/02* | (2006.01) | |

(52) U.S. Cl. .................... 514/322; 546/199; 514/395; 548/306.1

(58) Field of Classification Search ................ 514/322, 514/395; 546/199; 548/306.1
See application file for complete search history.

(56) References Cited

U.S. PATENT DOCUMENTS

| | | |
|---|---|---|
| 5,574,044 A | 11/1996 | Thompson et al. |
| 5,691,323 A | 11/1997 | Thompson et al. |
| 6,180,649 B1 | 1/2001 | Moldt et al. |
| 6,258,825 B1 | 7/2001 | Ozaki et al. |
| 6,423,725 B1 | 7/2002 | Ito et al. |

OTHER PUBLICATIONS

Powell, W.H. Pure & Applied Chemistry 1983, 55, 409-416.*
Hutchins, R. O. et. al. J.Org. Chem. 1977, 42, 82-91.*
Ciccocioppo, et. al. Psychopharmacology 2004, 172, 170-178.*
Gavioli, et. al. Nauyn-Schmiedberg's Arch. Pharmacol. 2006, 372, 319-300.*
Rizzi, et. al. Pain 2006, 124, 100-108.*
H. Kawamoto et al., Discovery of the First Potent and Selective Small Molecule Opioid Receptor-Like (ORL1)Antagonist:1-[(3R,4R)-1-Cyclooctylmethyl-3-Hydroxymethyl-4-Piperidyl]-3-Ethyl-1,3-Dihydro-2H-Benzimidazol-2-One (J-113397), J. of Medicinal Chemistry, vol. 42, No. 25, pp. 5061-5063, 1999.

* cited by examiner

*Primary Examiner*—Rita Desai
*Assistant Examiner*—David K O'Dell
(74) *Attorney, Agent, or Firm*—J. Eric Thies; William Krovatin

(57) ABSTRACT

The invention provides the compounds represented by the formula (I)

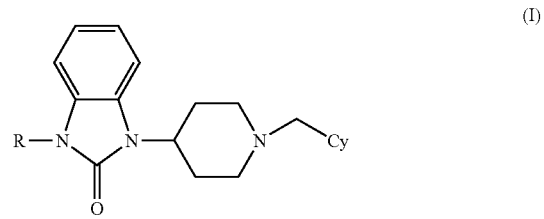

in which, R stands for a dihydroxy-substituted $C_1$-$C_6$ alkyl group, and Cy stands for an optionally substituted $C_6$-$C_{10}$ bi- or tri-cyclic aliphatic carbocyclic group. These compounds act as nociceptin receptor antagonist, and are useful, for example, as relievers against tolerance to narcotic analgesic, dependence on narcotic analgesic or addiction; analgesic enhancers; antiobestic or appetite suppressors; treating or prophylactic agents for cognitive impairment and dementia/amnesia; agents for treating developmental cognitive abnormality; remedy for schizophrenia; agents for treating neurodegenerative diseases; anti-depressant or treating agents for affective disorder; treating or prophylactic agents for diabetes insipidus; treating or prophylactic agents for polyuria; and remedy for hypotension and the like.

23 Claims, No Drawings

N-DIHYDROXYALKYL-SUBSTITUTED 2-OXO-IMIDAZOLE DERIVATIVES

CROSS REFERENCE TO RELATED APPLICATIONS

This application claims priority under 35 U.S.C. § 119 from JP Application No. JP2005-204264, filed Jul. 13, 2005 and U.S. Application No. 60/700,770, filed Jul. 20, 2005.

BACKGROUND OF THE INVENTION

This invention relates to substances which exhibit an antagonism to binding of nociceptin to nociceptin receptor ORL1 (Opioid receptor-like-1 receptor).

Compounds which inhibit binding of nociceptin to nociceptin receptor ORL1 are useful as analgesics against diseases accompanied with pain such as cancerous pain, postoperative pain, migraine, gout, chronic rheumatism, chronic pain and neuralgia; relievers against tolerance to narcotic analgesic represented by morphine; relievers against dependence on narcotic analgesic represented by morphine or against addiction; analgesic enhancers; antiobestic or appetite suppressors; treating or prophylactic agents for cognitive impairment and dementia/amnesia in aging, cerebrovascular diseases and Alzheimer's disease; agents for treating developmental cognitive abnormality in attention deficit, hyperactivity disorder and learning disability; remedy for schizophrenia; agents for treating neurodegenerative diseases represented by Parkinsonism and chorea; anti-depressant or treating agents for affective disorder; treating or prophylactic agents for diabetes insipidus; treating or prophylactic agents for polyuria; and remedy for hypotension and the like.

1. Field of the Invention

Nociceptin (the same substance as orphanin FQ) is a peptide consisting of 17 amino acid units having a similar structure to that of opioid peptide. Nociceptin has activity on reactivity against nociceptive stimulation, appetite stimulating activity, activity for reducing space learning ability, antagonism against analgesic action of classic opiate agonists, dopamine release inhibitory action, water diuresis action, vasodilative action and systemic blood pressure-lowering action, and it is considered to take part in intracerebral controlling of pain, appetite and memory learning through a nociceptin receptor ORL1 (cf. *Nature*, 377, 532 (1995); *Society for Neuroscience*, 22, 455 (1996); *NeuroReport*, 8, 423 (1997); *Eur. J. Neuroscience*, 9, 194 (1997); *Neuroscience*, 75, 1 (1996); ibid., 333 (1996); *Life Sciences*, 60, PL15 (1997); ibid., PL141 (1997); *Proceedings for National Academy of Sciences*, 94, 14858 (1997)).

Further, it is known that morphine tolerance is reduced or memory and learning ability are improved in knockout mice in which expression of nociceptin receptor ORL1 is inhibited (cf. *Neuroscience Letters*, 237, 136 (1997); *Nature*, 394, 577 (1998)).

It has also been reported that nociceptin itself induces symptoms resembling withdrawal symptoms observed with morphine addicts, and that non-peptide nociceptin receptor antagonist improves morphine tolerance, dependence and symptoms resembling withdrawal symptoms (cf. *Psychopharmacology*, 151, 344-350 (2000); *Journal of Neuroscience*, 20, 7640 (2000)).

On the other hand, nociceptin protein precursor-defective mice are reported to show behaviors resembling anxiety and changes in stress response (cf. *Proceedings for National Academy of Sciences*, 96, 10444 (1999)).

Hence substances which specifically inhibit binding of nociceptin to nociceptin receptor ORL1 are useful as analgesics against diseases accompanied with pain such as cancerous pain, postoperative pain, migraine, gout, chronic rheumatism, chronic pain and neuralgia; relievers against tolerance to narcotic analgesic represented by morphine; relievers against dependence on narcotic analgesic represented by morphine or against addiction; analgesic enhancers; antiobestic or appetite suppressors; treating or prophylactic agents for cognitive impairment and dementia/amnesia in aging, cerebrovascular diseases and Alzheimer's disease; agents for treating developmental cognitive abnormality in attention deficit, hyperactivity disorder and learning disability; remedy for schizophrenia; agents for treating neurodegenerative diseases represented by Parkinsonism and chorea; anti-depressant or treating agents for affective disorder, treating or prophylactic agents for diabetes insipidus; treating or prophylactic agents for polyuria; and remedy for hypotension and the like.

2. Description of Related Art

International Publication WO98/54168 or *J. Med. Chem.* 5061-5063 (1999) disclose compounds having antagonism to binding of nociceptin to nociceptin receptor ORL1. In particular, the compound of the following formula (A)

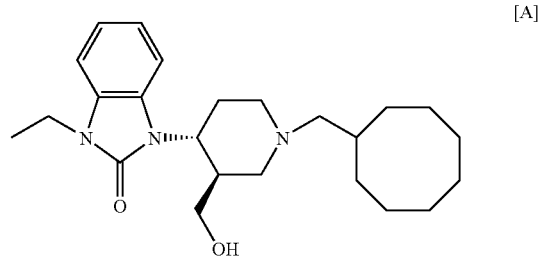

[A]

(hereinafter referred to as "Compound A") is disclosed as having excellent selective antagonism to binding of nociceptin to nociceptin receptor. Patent literature 1: International Publication WO98/54168. Non-patent literature 1: *J. Med. Chem.*, 1999, 5061-5063

BRIEF SUMMARY OF THE INVENTION

We have investigated compounds of analogous structures to that of Compound A in search for compounds which exhibit antagonistic activity to binding of nociceptin to nociceptin receptor ORL1, to discover that those compounds having bi- or tricyclic aliphatic carbocyclic group of specific carbon numbers in place of the cyclooctyl group and also having dihydroxyalkyl substituent group on the nitrogen atom possess well balanced activities of not only selectively inhibiting binding of nociceptin to nociceptin receptor, but also exhibiting excellent in vivo metabolic properties, and can be compounds particularly suitable for application to human being. The present invention is completed based on that discovery.

DETAILED DESCRIPTION OF THE INVENTION

The present invention provides (1) 2-oxoimidazole derivatives represented by the formula (I)

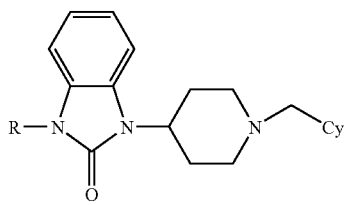

in which R stands for a dihydroxy-substituted $C_1$-$C_6$ alkyl group, and Cy stands for an optionally substituted $C_6$-$C_{10}$ bi- or tricyclic aliphatic carbocyclic group or their pharmaceutically acceptable salts.

The invention furthermore provides (2) pharmaceutical preparations comprising pharmaceutically acceptable adjuvants and an effective amount of a compound as described in (1) above or a pharmaceutically acceptable salt thereof; and (3) analgesics; relievers against tolerance to narcotic analgesic represented by morphine; relievers against dependence on narcotic analgesic represented by morphine or against addiction; analgesic enhancers; antiobestic or appetite suppressors; treating or prophylactic agents for cognitive impairment and dementia/amnesia in aging, cerebrovascular diseases and Alzheimer's disease; agents for treating developmental cognitive abnormality in attention deficit, hyperactivity disorder and learning disability; remedy for schizophrenia; agents for treating neurodegenerative diseases represented by Parkinsonism and chorea; anti-depressant or treating agents for affective disorder; treating or prophylactic agents for diabetes insipidus; treating or prophylactic agents for polyuria; and remedy for hypotension; which comprise a compound as described in (1) above or a pharmaceutically acceptable salt thereof as the active ingredient.

Hereinafter the invention is explained in details, referring to specific examples.

In the formula (I), R stands for a $C_1$-$C_6$ alkyl group having two hydroxyl groups, specific examples including 2-hydroxy-1-(hydroxymethyl)ethyl, 2,3-dihydroxypropyl, 2,3-dihydroxy-2-methylpropyl, 2,3-dihydroxybutyl, 2,4-dihydroxybutyl, 3,4-dihydroxybutyl, 2,3-dihydroxy-1-methylpropyl, 2-hydroxy-1-(hydroxymethyl)propyl, 3-hydroxy-1-(hydroxymethyl)propyl, 3-hydroxy-2-hydroxymethyl)propyl, 2,3-dihydroxypentyl, 2,4-dihydroxypentyl, 2,5-dihydroxypentyl, 3,4-dihydroxypentyl, 3,5-dihydroxypentyl, 4,5-dihydroxypentyl, 2,3-dihydroxy-1-methylbutyl, 2,4-dihydroxy-1-methylbutyl, 3,4-dihydroxy-1-methylbutyl, 2-hydroxy-1-(hydroxymethyl)butyl, 3-hydroxy-1-(hydroxymethyl)butyl, 4-hydroxy-1-(hydroxymethyl)butyl, 2,3-dihydroxy-2-methylbutyl, 2,4-dihydroxy-2-methylbutyl, 3,4-dihydroxy-2-methylbutyl, 2-hydroxy-2-(hydroxymethyl)butyl, 3-hydroxy-2-(hydroxymethyl)butyl, 4-hydroxy-2-(hydroxymethyl)butyl, 2,3-dihydroxy-3-methylbutyl, 2,4-dihydroxy-3-methylbutyl, 3,4-dihydroxy-3-methylbutyl, 4-hydroxy-3-(hydroxymethyl)butyl, 2,3-dihydroxy-1,1-dimethylpropyl, 2-hydroxy-1 hydroxymethyl) 1-methylpropyl, 3-hydroxy-1-(hydroxymethyl)-1-methylpropyl, 1,1-bis(hydroxymethyl)propyl, 2,3-dihydroxy-1,2-dimethylpropyl, 2-hydroxy-1-(hydroxymethyl)-2-methylpropyl, 3-hydroxy-2-(hydroxymethyl)-2-methylpropyl, 2,3-dihydroxy-1-ethylpropyl, 2-hydroxy-1-(2-hydroxyethyl)propyl, 2-hydroxy-1-(1-hydroxyethyl)propyl, 3-hydroxy-1-(2-hydroxyethyl)propyl, 2,3-dihydroxyhexyl, 2,4-dihydroxyhexyl, 2,5-dihydroxyhexyl, 2,6-dihydroxyhexyl, 3,4-dihydroxyhexyl, 3,5-dihydroxyhexyl, 3,6-dihydroxyhexyl, 4,5-dihydroxyhexyl and 4,6-dihydroxyhexyl. Preferred examples are $C_3$-$C_4$ alkyl groups having two hydroxyl group and, in particular, 2,3-dihydroxypropyl, 2-hydroxy-1-(hydroxymethyl)ethyl and 2,3-dihydroxy-2-methylpropyl groups are recommended.

Cy stands for an optionally substituted $C_6$-$C_{10}$ bi- or tricyclic aliphatic carbocyclic group.

As the "substituent" in "optionally substituted $C_6$-$C_{10}$ bi- or tricyclic aliphatic carbocyclic group", for example, halogen such as fluorine, chlorine and the like and $C_1$-$C_6$ alkyl groups such as methyl, ethyl, n-propyl, isopropyl, n-butyl, n-penty and the like can be named. Preferably, $C_1$-$C_4$ alkyl groups are recommended.

"$C_6$-$C_{10}$ bi- or tri-cyclic aliphatic carbocyclic groups" signify saturated aliphatic carbocyclic groups which are bi- or tricyclic groups. For example, spiro[2.5]oct-4-yl, spiro[2.5]oct-5-yl, spiro[2.5]oct-6-yl, spiro[3.5]non-5-yl, spiro[3.5]non-6-yl, spiro[3.5]non-7-yl, spiro[4.5]dec-6-yl, spiro[4.5]dec-7-yl, spiro[4.5]dec-8-yl, bicyclo[2.2.1]hept-2-yl, bicyclo[2.2.2]oct-2-yl, 1-spiro(bicyclo[2.2.1]heptane-2,1'-cyclopropan)-3-yl, 1-spiro(bicyclo[2.2.1]heptane-2,1'-cyclopropan)-5-yl, 1-spiro(bicyclo[2.2.1]-heptane-2,1'-cyclopropan)-6-yl and the like are named.

As specific examples of Cy, spiro[2.5]oct-4-yl, spiro[2.5]oct-5-yl, spiro-[2.5]oct-6-yl, spiro[3.5]non-5-yl, spiro[3.5]non-6-yl, spiro[3.5]non-7-yl, spiro[4.5]dec-6-yl, spiro[4.5]dec-7-yl, spiro[4.5]dec-8-yl, bicyclo[2.2.1]hept-2-yl, 3,3-dimethylbicyclo[2.2.1]hept-2-yl, 3,3-dimethylbicyclo[2.2.1]hept-5-yl, 3,3-dimethylbicyclo[2.2.1]hept-6-yl, bicyclo[2.2.2]oct-2-yl, 1-spiro(bicyclo[2.2.1]heptane-2,1'-cyclopropan)-3-yl, 1-spiro(bicyclo[2.2.1]-heptane-2,1'-cyclopropan)-5-yl, 1-spiro(bicyclo[2.2.1]heptane-2,1'-cyclopropan)-6-yl and the like can be named. Preferably, spiro[4.5]dec-6-yl, spiro[2.5]oct-4-yl, spiro[3.5]non-5-yl, 3,3-dimethylbicyclo[2.2.1]hept-2-yl, 1-spiro(bicyclo[2.2.1]heptane-2,1'-cyclopropan)-3-yl and the like are recommended.

According to the invention, by the adoption of those 2-oxoimidazole derivatives having on its 1-position nitrogen atom a dihydroxyalkyl group and furthermore having as Cy an optionally substituted $C_6$-$C_{10}$ bi- or tri-cyclic aliphatic carbocyclic group, compounds having very well balanced physiological activity of excellent antagonism to nociceptin receptor and also excellent metabolic stability can be provided.

As specific examples of the compounds represented by the formula (I), the following can be named:

1) 1-(2,3-dihydroxypropyl)-3-[1-spiro[4.5]-dec-6-ylmethyl]-piperidin-4-yl]-1,3-dihydro-2H-benzimidazol-2-one, 2) 1-[(2R)-2,3-dihydroxypropyl]-3-{1-[(6S)-spiro[4.5]dec-6-ylmethyl]piperidin-4-yl}-1,3-dihydro-2H-benzimidazol-2-one, 3) 1-[(2R)-2,3-dihydroxypropyl]-3-{1-[(6R)-spiro[4.5]dec-6-ylmethyl]piperidin-4-yl}-1,3-dihydro-2H-benzimidazol-2-one, 4) 1-[(2S)-2,3-dihydroxypropyl]-3-{1-[(6S)-spiro[4.5]dec-6-ylmethyl]piperidin-4-yl}-1,3-dihydro-2H-benzimidazol-2-one, 5) 1-[(2S)-2,3-dihydroxypropyl]-3-{1-[(6R)-spiro[4.5]dec-6-ylmethyl]piperidin-4-yl}-1,3-dihydro-2H-benzimidazol-2-one, 6) 1-(2,3-dihydroxypropyl)-3-[1-(spiro-[3.5]non-5-ylmethyl)-piperidin-4-yl]-1,3-dihydro-2H-benzimidazol-2-one, 7) 1-[(2R)-2,3-dihydroxypropyl]-3-{1-[(5S)-spiro[3.5]non-5-ylmethyl]piperidin-4-yl}-1,3-dihydro-2H-benzmidazol-2-one, 8) 1-[(2R)-2,3-dihydroxypropyl]-3-{1-[(5R)-spiro[3.5]non-5-ylmethyl]piperidin-4-yl}-1,3-dihydro-2H-benzimidazol-2-one, 9) 1-[(2S)-2,3-dihydroxypropyl]-3-{1-[(5S)spiro[3.5]non-5-ylmethyl]piperidin-4-yl}-1,3-dihydro-2H-benzimidazol-2-one, 10) 1-[(2S)-2,3-dihydroxypropyl]-3-{1-[(5R)-spiro[3.5]non-5-ylmethyl]piperidin-4-yl}-1,3-dihydro-2H-benzimidazol-2-one, 11) 1-(2,3-dihydroxypropyl)-3-{1-[(3,3-dimethylbicyclo[2.2.1]-hept-2-yl)methyl]piperidin-4-yl}-1,3-dihydro-2H-benzimidazol-2-one, 12) 1-[(2R)-2,3-dihydroxypropyl]-3-(1-{[(1S,2S,4R)-3,3-dimethylbicyclo[2.2.1]hept-2-yl]methyl}piperidin-4-yl)-1,3-dihydro-2H-benzimidazol-2-one, 13) 1-[(2R)-2,3-dihydroxypropyl]-3-(1-{[(1S,2R,4R)-3,3-dimethylbicyclo[2.2.1]hept-2-yl]methyl}piperidin-4-yl)-1,3-dihydro-2H-benzimidazol-2-one, 14) 1-[(2R)-2,3-dihydroxypropyl]-3-(1-{[(1R,2R,4S)-3,3-dimethylbicyclo[2.2.1]hept-2-yl]methyl}piperidin-4-yl)-1,3-dihydro-2H-benzimidazol-2-one, 15) 1-[(2R)-2,3-dihydroxypropyl]-3-(1-{[(1R,2S,4S)-3,3-dimethylbicyclo[2.2.1]hept-2-yl]methyl}piperidin-4-yl)-1,3-dihydro-2H-benzimidazol-2-one, 16) 1-[(2S)-2,3-dihydroxypropyl]-3-(1-{[(1S,2S,4R)-3,3-dimethylbicyclo[2.2.1]hept-2-yl]methyl}piperidin-4-yl)-1,3-dihydro-2H-benzimidazol-2-one, 17) 1-[(2S)-2,3-dihydroxypropyl]-3-(1-{[(1S,2R,4R)-3,3-dimethylbicyclo[2.2.1]hept-2-yl]methyl}piperidin-4-yl)-1,3-dihydro-2H-benzimidazol-2-one, 18) 1-[(2S)-2,3-dihydroxypropyl]-3-(1-{[(1R,2R,4S)-3,3-dimethylbicyclo[2.2.1]hept-2-yl]methyl}piperidin-4-yl)-1,3-dihydro-2H-benzimidazol-2-one, 19) 1-[(2S)-2,3-dihydroxypropyl]-3-(1-{[(1R,2S,4S)-3,3-dimethylbicyclo[2.2.1]hept-2-yl]methyl}piperidin-4-yl)-1,3-dihydro-2H-benzimidazol-2-one, 20) 1-(2,3-dihydroxypropyl)-3-[1-(spiro[2.5]oct-4-ylmethyl)-piperidin-4-yl]-1,3-dihydro-2H-benzimidazol-2-one, 21) 1-[(2R)-2,3-dihydroxypropyl]-3-{1-[(4S)-spiro[2.5]oct-4-ylmethyl]piperidin-4-yl}-1,3-dihydro-2H-benzimidazol-2-one, 22) 1-[(2R)-2,3-dihydroxypropyl]-3-{1-[(4R)-spiro[2.5]oct-4-ylmethyl]piperidin-4-yl}-1,3-dihydro-2H-benzimidazol-2-one, 23) 1-[(2S)-2,3-dihydroxypropyl]-3-{1-[(4S)-spiro[2.5]oct-4-ylmethyl]piperidin-4-yl}-1,3-dihydro-2H-benzimidazol-2-one, 24) 1-[(2S)-2,3-dihydroxypropyl]-3-{1-[(4R)-spiro[2.5]oct-4-ylmethyl]piperidin-4-yl}-1,3-dihydro-2H-benzimidazol-2-one, 25) 1-(2,3-dihydroxypropyl)-3-[1-(spiro[bicyclo[2.2.1]heptane-2,1'-cyclopropan]-3-ylmethyl)piperidin-4-yl]-1,3-dihydro-2H-benzimidazol-2-one, 26) 1-[(2R)-2,3-dihydroxypropyl]-3-{1-[(1R,3S,4S)-spiro[bicyclo[2.2.1]heptane-2,1'-cyclopropan]-3-ylmethyl]piperidin-4-yl}-1,3-dihydro-2H-benzimidazol-2-one, 27) 1-[(2R)-2,3-dihydroxypropyl]-3-{1-[(1R,3R,4S)-spiro[bicyclo[2.2.1]heptane-2,1'-cyclopropan]-3-ylmethyl]piperidin-4-yl}-1,3-dihydro-2H-benzimidazol-2-one, 28) 1-[(2R)-2,3-dihydroxypropyl]-3-{1-[(1S,3R,4R)-spiro[bicyclo[2.2.1]heptane-2,1'-cyclopropan]-3-ylmethyl]piperidin-4-yl}-1,3-dihydro-2H-benzimidazol-2-one, 29) 1-[(2R)-2,3-dihydroxypropyl]-3-{1-[(1S,3S,4R)-spirobicyclo[2.2.1]heptane-2,1'-cyclopropan]-3-ylmethyl]piperidin-4-yl}-1,3-dihydro-2H-benzimidazol-2-one, 30) 1-[(2S)-2,3-dihydroxypropyl]-3-{1-[(1R,3S,4S)-spiro[bicyclo[2.2.1]heptane-2,1'-cyclopropane]-3-ylmethyl]piperidin-4-yl}-1,3-dihydro-2H-benzimidazol-2-one, 31) 1-[(2S)-2,3-dihydroxypropyl]-3-{1-[(1R,3R,4S)-spiro[bicyclo[2.2.1]heptane-2,1'-cyclopropan]-3-ylmethyl]piperidin-4-yl}-1,3-dihydro-2H-benzimidazol-2-one, 32) 1-[(2S)-2,3-dihydroxypropyl]-3-{1-[(1S,3R,4R)-spiro[bicyclo[2.2.1]heptane-2,1'-cyclopropan]-3-ylmethyl]piperidin-4-yl}-1,3-dihydro-2H-benzimidazol-2-one, 33) 1-[(2S)-2,3-dihydroxypropyl]-3-{1-[(1S,3S,4R)-spiro[bicyclo[2.2.1]heptane-2,1'-cyclopropan]-3-ylmethyl]piperidin-4-yl}-1,3-dihydro-2H-benzimidazol-2-one, 34) 1-[2-hydroxy-1-(hydroxymethyl)ethyl]-3-[1-(spiro[2.5]-oct-4-ylmethyl)piperidin-4-yl]-1,3-dihydro-2H-benzimidazol-2-one, 35) 1-[2-hydroxy-1-(hydroxymethyl)ethyl]-3-{1-[(4R)-spiro-[2.5]oct-4-ylmethyl]piperidin-4-yl}-1,3-dihydro-2H-benzimidazol-2-one, 36) 1-[2-hydroxy-1-(hydroxymethyl)ethyl]-3-{1-[(4S)-spiro[2.5]-oct-4-ylmethyl]piperidin-4-yl}-1,3-dihydro-2H-benzimidazol-2-one, 37) 1-[2-hydroxy-1-(hydroxymethyl)ethyl-3-[1-(spiro[bicyclo-[2.2.1]heptane-2,1'-cyclopropan]-3-ylmethyl)piperidin-4-yl]-1,3-dihydro-2H-benzimidazol-2-one, 38) 1-[2-hydroxy-1-(hydroxymethyl)ethyl]-3-{1-[(1R,3S,4S)-spiro[bicyclo[2.2.1]heptane-2,1'-cyclopropan]-3-ylmethyl]piperidin-4-yl}-1,3-dihydro-2H-benzimidazol-2-one, 39) 1-[2-hydroxy-1-(hydroxymethyl)ethyl]-3-{1-[(1R,3R,4S)-spiro[bicyclo[2.2.1]heptane-2,1'-cyclopropan]-3-ylmethyl]piperidin-4-yl}-1,3-dihydro-2H-benzimidazol-2-one, 40) 1-[2-hydroxy-1-(hydroxymethyl)ethyl]-3-{1-[(1S,3R,4R)-spiro[bicyclo[2.2.1]heptane-2,1'-cyclopropan]-3-ylmethyl]piperidin-4-yl}-1,3-dihydro-2H-benzimidazol-2-one, 41) 1-[2-hydroxy-1-(hydroxymethyl)ethyl]-3-{1-[(1S,3S,4R)-spiro[bicyclo[2.2.1]heptane-2,1'-cyclopropan]-3-ylmethyl]piperidin-4-yl}-1,3-dihydro-2H-benzimidazol-2-one, 42) 1-(2,3-dihydroxy-2-methylpropyl)-3-[1-(spiro[2.5]oct-4-ylmethyl)piperidin-4-yl]-1,3-dihydro-2H-benzimidazol-2-one, 43) 1-[(2R)-2,3-dihydroxy-2-methylpropyl]-3-{1-[(4S)-spiro[2.5]-oct-4-ylmethyl]piperidin-4-yl}-1,3-dihydro-2H-benzimidazol-2-one, 44) 1-[(2R)-2,3-dihydroxy-2-methylpropyl]-3-{1-[(4R)-spiro[2.5]-oct-4-ylmethyl]piperidin-4-yl}-1,3-dihydro-2H-benzimidazol-2-one, 45) 1-[(2S)-2,3-dihydroxy-2-methylpropyl]-3-{1-[(4S)-spiro[2.5]-oct-4-ylmethyl]piperidin-4-yl}-1,3-dihydro-2H-benzimidazol-2-one, and 46) 1-[(2S)-2,3-dihydroxy-2-methylpropyl]-3-{1-[(4R)-spiro[2.5]-oct-4-ylmethyl]piperidin-4-yl}-1,3-dihydro-2H-benzimidazol-2-one.

Preferably,

1-[(2R)-2,3-dihydroxypropyl]-3-{(1R,3S,4S)-spiro[bicyclo-[2.2.1]heptane-2,1'-cyclopropan]-3-ylmethyl]piperidin-4-yl}-1,3-dihydro-2H-benzimidazol-2-one, 1-[(2S or 2R)-2,3-dihydroxy-2-methylpropyl-3-{1-[(4S)-spiro[2.5]oct-4-ylmethyl]piperidin-4-yl}-1,3-dihydro-2H-benzimidazol-2-one, 1-[2-hydroxy-1-(hydroxymethyl)ethyl]-3-{1-[(1R,3S,4S)-spiro-[bicyclo[2.2.1]heptane-2,1'-cyclopropan]-3-ylmethyl]piperidin-4-yl}-1,3-dihydro-2H-benzimidazol-2-one, 1-[(2R)-2,3-dihydroxypropyl]-3-{1-[(4S)-spiro[2.5]oct-4-ylmethyl]piperidin-4-yl}-1,3-dihydro-2H-benzimidazol-2-one and 1-[(2R)-2,3-dihydroxypropyl]-3-[1-[(6S or 6R)-spiro[4.5]dec-6-ylmethyl]piperidin-4-yl}-1,3-dihydro-2H-benzimidazol-2-one are recommended.

Production Processes of the Compounds Represented by the Formula (I)

Those compounds represented by the formula (I) can be prepared by following production processes or also by the processes as described in WO98/54168.

Production Process 1

Production process 1 uses 1,3-dihydro-1-(4-piperidinyl)-2H-benzimidazol-2-one which is a known compound, and provides compounds of the formula (I) through three- or four-stage steps.

reaction scheme 1

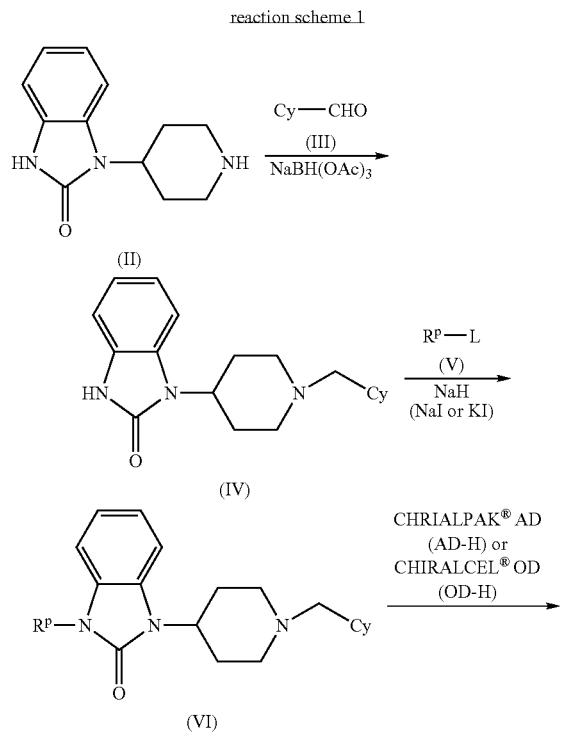

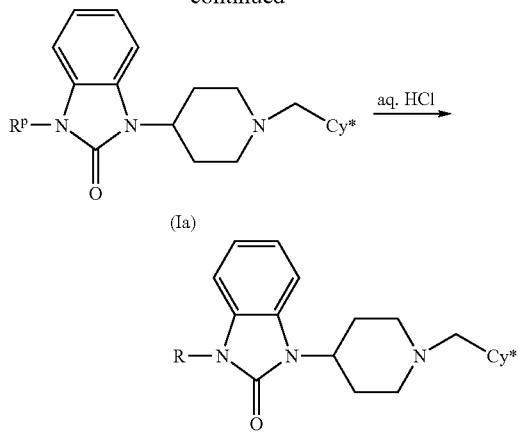

in which, $R^p$ stands for a lower alkyl group having two protected hydroxyl groups, L stands for a leaving group, Cy* stands for an optically active Cy, and Cy and R have the same significations as defined earlier.

A compound of the formula (II) and a compound of the formula (III) are subjected to a reductive alkylation reaction in an organic solvent in the presence of a reducing agent, to provide a compound of the formula (IV).

As the equivalents of the compounds of the formulae (II) and (III), respectively, they are normally used in equimolar amounts, or either one of them is used in slight molar excess.

As the reducing agent, for example, sodium cyanoborohydride, sodium triacetoxyborohydride, zinc biscyanoborohydride, nickel biscyanoborohydride and the like can be named.

As the equivalents of the reducing agent, it may be a mol to molar excess, preferably 1-5 mols, per mol of the compound represented by the formula (II).

The reaction is normally carried out in organic solvent. Examples of useful solvent include alcohols such as methanol, ethanol and propanol; ethers such as diethyl ether, tetrahydrofuran ("THF") and dioxane; halogenated hydrocarbons such as methylene chloride, chloroform and dichloroethane; aromatic hydrocarbons such as benzene, toluene, chlorobenzene and xylene; and aprotic polar solvents such as dimethylformamide ("DMF"), acetonitrile and hexamethylphosphorictriamide, or mixed solvents of the foregoing.

Exemplary reaction temperature normally ranges—20° C.-100° C., preferably 0° C.—room temperature, and the reaction time ranges normally from 5 minutes to 7 days, preferably 1-6 hours.

As the compounds represented by the formula (III), for example, the following compounds can be used.

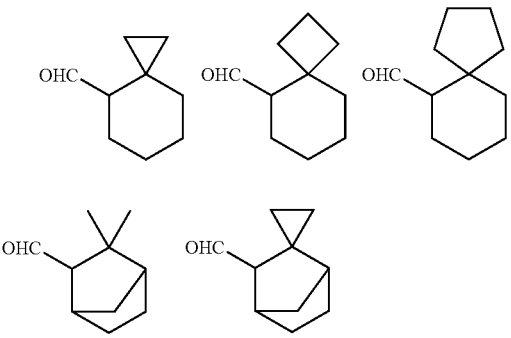

Then the compound of the formula (IV) is condensed with a compound of the formula (V) in an organic solvent in the presence of a base, to provide a compound of the formula (VI).

As the equivalents of the compound of the formula (V), it may range from a mol to molar excess, preferably 1-5 mols, per mol of the compound of the formula (IV).

Examples of useful base include sodium hydride, potassium hydride, lithium hexamethyldisilazide, sodium hexamethyldisilazide, potassium hexamethyldisilazide, potassium carbonate and sodium carbonate. Preferably, sodium hydride and potassium hydride are recommended.

As the equivalents of such a base, for example, it may range from a mol to molar excess, preferably 1-5 mols, per mol of the compound of the formula (V).

An alkali metal halide such as sodium iodide, potassium iodide or the like may be added to the reaction system for promoting the reaction. As the equivalents in such an occasion, for example, 0.1 mol—molar excess of an alkali metal halide per mol of the compound of the formula (IV) can be used.

As the organic solvent, for example, DMF, THF, hexamethylphosphorictriamide and the like can be named.

Exemplary reaction temperature normally ranges 0° C.-150° C., preferably room temperature—130° C. being recommended. The reaction time normally ranges 5 minutes to 7 days, preferably an hour—12 hours.

In the compound of the formula (V), L stands for a leaving group which can be, for example, benzenesulfonyloxy, p-toluenesulfonyloxy, methanesulfonyloxy, fluorine, chlorine or bromine.

Specific examples of the compounds represented by the formula (V) include the following.

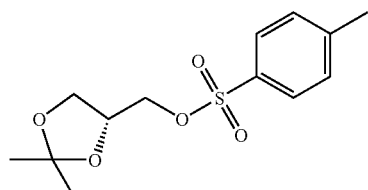

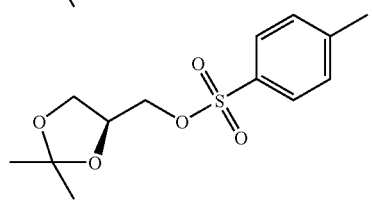

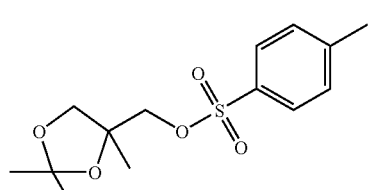

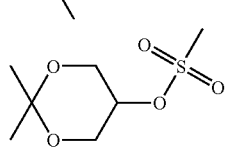

Successively the compound of the formula (VI) is optically resolved with optically active column, where necessary, to provide an optically active compound of the formula (Ia), and then the protective groups of the hydroxyl groups in the compound of the formula (Ia) are removed to provide a compound of the formula (I).

Such hydroxyl-protective groups are subject to no particular limitation, so long as they have the required function. For example, such groups as tert-butyl; alkylsilyl, e.g., trimethylsilyl, tert-butyldimethylsilyl and tert-butyldiphenylsilyl; methoxymethyl; tetrahydropyranyl; trimethylsilylethoxymethyl; aralkyl, e.g., benzyl, p-methoxybenzyl, 2,3-dimethoxybenzyl, o-nitrobenzyl, p-nitrobenzyl and trityl; and acyl, e.g., formyl and acetyl can be named, among which methoxymethyl, tetrahydropyranyl, trityl, trimethylsilylethoxymethyl, tert-butyldimethylsilyl and acetyl are particularly preferred.

In particular, as protective groups of 1,2- or 1,3-diols, for example, methyleneketal, ethylideneacetal, phenylethylideneacetal, 4-methoxyphenylethylideneacetal, isopropylideneketal and benzylideneacetal can be named.

Means for removing protective groups differ depending on kind of protective groups and stability of individual compounds represented by formula [Ia]. For example, the removal is conducted following those methods describe in literature (cf. Protective Groups in Organic Synthesis, T. W. Greene, John Wiley & Sons Co., (1981)) or those analogous thereto, by solvolysis using acid or base, i.e., a method of having, for example, from 0.01 mol to a large molar excess of acid, preferably trifulroacetic acid, formic acid, hydrochloric acid or the like; or from equimolar to a large molar excess of base, preferably potassium hydroxide, calcium hydroxide or the like, act on the object compound; chemical reduction using hydrogenated metal complex or by catalytic reduction using palladium-on-carbon catalyst or Raney nickel catalyst.

In case of diol-protective groups such as ketal, acetal and the like, the deprotection can be effected by hydrolyzing the compound of the formula (VI) using hydrochloric acid, in a solvent such as THF, dioxane or the like, at room temperature—100° C.

Where necessary, the compound of the formula (VI) can be optically resolved by means of chromatography using optically active column, to provide an optically active compound of the formula (Ia).

As the optically active column, for example CHIRALPAK® AD, CHIRALPAK® AD-H, CHIRAL CELL® OD and CHIRAL CELL® OD-H (Daicel Co., Ltd.) can be named.

As the eluent solvent in that occasion, mixed solvents such as hexane/2-propanol/diethylamine=1900/100/2–800/200/1 by volume, or hexane/ethanol/diethylamine=1900/100/2–800/200/1 by volume can be used.

As the detection means of the compounds in such occasion, for example, ultraviolet rays in the wavelength region near 280 nm may be used.

Production Process 2

Production process 2 is one for making compounds of the formula (I), using the formula (IV) compounds as the starting material.

reaction scheme 2

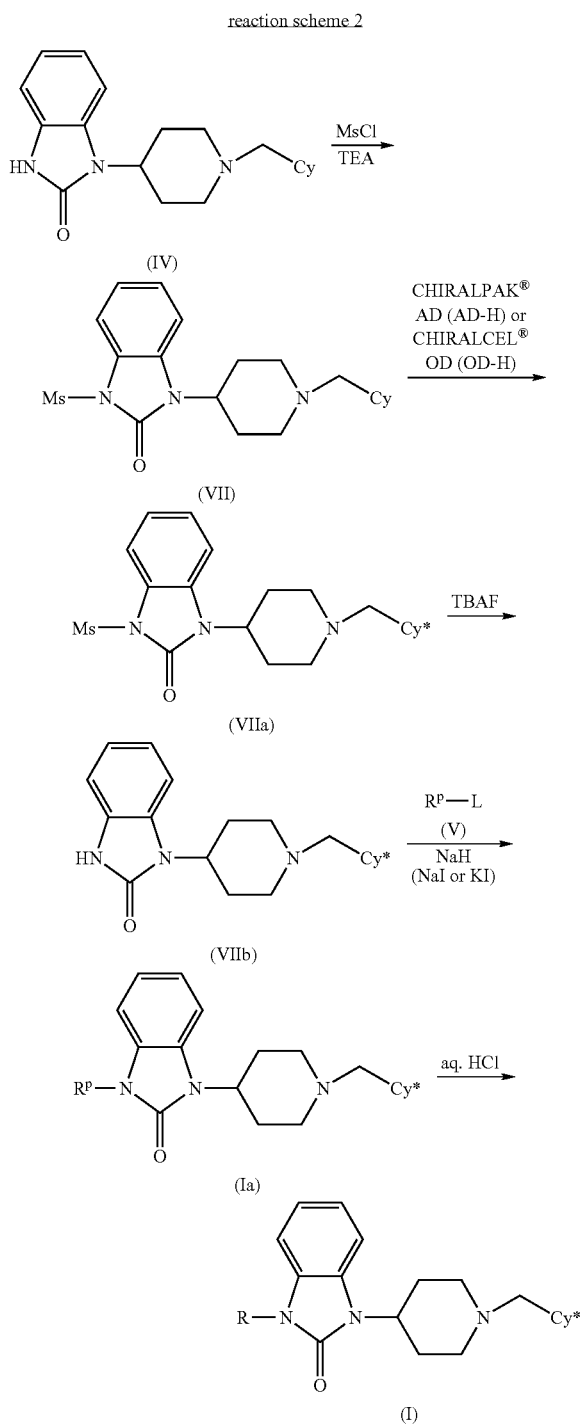

in which, Ms stands for methanesulfonyl group, TEA stands for triethylamine, and Cy, Cy*, R$^p$, L and R have the sane significations as previously defined.

A compound of the formula (IV) is mesylated by a means known per se, to be converted to a compound of the formula (VII) which is successively optically resolved according to the production process 1 to provide a compound of the formula (VIIa). Further, the mesyl group in a compound of the formula (VIIa) is removed using tetra-n-butylammonium fluoride (TBAF) to provide a compound of the formula (VIIb) which is reacted with the compound of the formula (V) according to the production process 1 to provide the compound of the formula (Ia) which is further converted to the compound of the formula (I) by deprotection.

So obtained, compound of the formula (I) can be easily isolated and purified by ordinary separation means, for example, solvent extraction, recrystallization, column chromatography, preparative thin layer chromatography or the like.

These compounds can be converted to pharmaceutically acceptable salts according to accepted practice. Conversely, conversion from salts to free compounds can also be conducted by conventionally practiced means.

As examples of salts of compounds of the formula (I), acid addition salts at the piperidinyl group can be named.

As examples of such acid addition salts, inorganic acid salts such as hydrochloride, sulfate, nitrate, phosphate, perchlorate and the like; carboxylic acid salts such as maleate, fumarate, tartrate, citrate, ascorbate, trifluoroacetate and the like; and sulfonates such as methanesulfonate, isethionate, benzenesulfonate, p-toluenesulfonate and the like can be named.

Action of compounds of the present invention as nociceptin receptor antagonist is shown, for example, by the following pharmacological test examples.

Pharmacological Test Example 1 (Nociceptin Receptor Binding Inhibition Assay)

cDNA which codes a human nociceptin receptor gene was integrated with an expression vector pCR3 (Invitrogen) to prepare pCR3/ORL1. Next, pCR3/ORL1 was transfected in CHO cells using a transfectam (Nippongene) to obtain a stable expression strain (CHO/ORL1 cells) having resistance against 1 mg/ml G418. Membrane fractions were prepared from this stable expression strain to carry out a receptor binding assay. The membrane of 11 μg, 50 pM [$^{125}$I] Tyr$^{14}$-Nociceptin (Amersham Pharmacia), 1 mg Wheatgerm agglutinin SPA beads (PVT based; Amersham Pharmacia) and each test compound were suspended in an NC buffer (50 mM Hepes, 10 mM sodium chloride, 1 mM magnesium chloride, 2.5 mM calcium chloride, 0.1% BSA, 0.025% bacitracin, pH 7.4) and incubated at 37° C. for 60 minutes, and then the radioactivity was determined. The binding activity to the nociceptin receptor was indicated by the 50% inhibition concentration (IC$_{50}$ value) of [$^{125}$I] Tyr$^{14}$-Nociceptin binding of each test compound. The results were as shown in Table 1.

TABLE 1

| Compound | IC$_{50}$ value (nM) |
|---|---|
| Example 1 | 1.6 |
| Example 2 | 5.1 |
| Example 3 | 8.7 |
| Example 4 | 1.9 |
| Example 5 | 2.8 |

Pharmacological Test Example 2 (Antagonism Against Nociceptin-Elicited G Protein Activation)

CHO cells which stably represented nociceptin receptor ORL1 were used to investigate the action of each test compound against nociceptin-elicited G protein activation. A membrane prepared from the CHO/ORL1 cells, 50 nM nociceptin, 200 pM GTPγ[$^{35}$S] (NEN), 1.5 mg Wheatgerm agglutinin SPA beads (Amersham Pharmacia) and each of the test compounds were mixed in a GDP buffer (20 mM Hepes, 100 mM sodium chloride, 10 mM magnesium chloride, 1 mM EDTA, 5 µM GDP, pH 7.4) and incubated at 25° C. for 150 minutes, and then the radioactivity was determined. The antagonism against nociceptin-elicited G protein activation was shown by the 50% inhibition concentration ($IC_{50}$ value) of each test compound against GTPγ[$^{35}$S] binding. The results were as shown in Table 2.

TABLE 2

| Compound | 50% value (nM) |
| --- | --- |
| Example 1 | 3.9 |
| Example 2 | 8.6 |
| Example 3 | 18.0 |
| Example 4 | 6.0 |
| Example 5 | 4.5 |

Pharmacological Test Example 3 (Metabolic Stability Test)

Metabolic stability of test compounds was examined using human liver microsome. A 100 mM potassium phosphate buffer (pH 7.4) comprising 10 mM G-6-P, 1.0 mM NADP$^+$, 10 units/mL G-6-P DH, 3.0 mM MgCl$_2$ and 0.25 mg protein/mL of human liver microsome was prepared, each 392 µL of which was poured into plural vessels and preincubated at 37° C. for 5 minutes. Then 8 µL each of 50 µM test compound (50% acetonitrile solution) was added to initiate the reaction (final test compound concentration: 1 µM). At the initiation time and 30 minutes thereafter of the reaction, 150 µL of each reaction solution was added to 450 µL of ethanol to suspend the reaction, followed by centrifugal separation (12,000 g, 12 minutes, 4° C.). Resulting supernatant was analyzed with LC/MS/MS. Based on the peak area of the test compound in each sample at the initiating time of the reaction as 100%, the test compound's residual ratio in the sample after 30 minutes' reaction was calculated. The results were as shown in Table 3.

Residual ratio(%)=

[peak area(after 30 minutes' reaction)/ peak area(0 minute's reaction)]×100.

TABLE 3

| Compound | Residual Ratio (%) |
| --- | --- |
| Example 2 | 82 |
| Example 4 | 72 |
| Example 5 | 65 |

Pharmaceutical Preparations Comprising Compounds Represented by the Formula (I)

The compounds of the present invention can be administered orally or parenterally and, as formulated into preparation forms suitable for such administration routes, can be used as analgesics against diseases accompanied by pain such as cancerous pain, postoperative pain, migraine, gout, chronic rheumatism, chronic pain and neuralgia; relievers against tolerance to narcotic analgesic represented by morphine; relievers against dependence on narcotic analgesic represented by morphine or against addiction; analgesic enhancer; antiobestic or appetite suppressors; treating or prophylactic agents for cognitive impairment and dementia/amnesia in aging, cerebrovascular diseases and Alzheimer's disease; agents for treating developmental cognitive abnormality in attention deficit, hyperactivity disorder and learning disability; remedy for schizophrenia; agents for treating neurodegenerative diseases represented by Parkinsonism and chorea; anti-depressants or treating agents for affective disorder; treating or prophylactic agents for diabetes insipidus; treating or prophylactic agents for polyuria; remedy for hypotension, and the like.

In actually using the compounds of the present invention clinically, they can normally be formulated into various preparation forms suitable for individual mode of administration, with pharmaceutically acceptable adjuvants. As the adjuvants, various additives customarily used in the field of medical preparations can be used, examples of which including gelatin, lactose, sucrose, titanium oxide, starch, crystalline cellulose, hydroxypropylmethyl cellulose, carboxymethyl cellulose, corn starch, microcrystalline wax, white petrolatum, magnesium aluminate metasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, acacia, propylene glycol, polyalkylene glycol, cyclodextrin or hydroxypropyl cyclodextrin and the like.

As the forms of preparations formulated as pharmaceutical compositions using these adjuvants, solid preparations such as tablets, capsules, granules, powders and suppositories; liquid preparations such as syrups, elixirs and injections can be named. These preparations can be formulated according to conventional methods used in the field of pharmaceutics. Liquid preparations may be in a form which is dissolved or suspended in water or other suitable medium immediately prior to use. In particular, injections may be in the form of a solution or suspension in physiological saline solution or a glucose solution, to which a buffer agent, a preservative or the like may be added.

These preparations can contain a compound or compounds of the present invention at the ratios of 1-100 wt %, preferably 1-60 wt %, based on the total pharmaceutical preparation. These preparations may further contain other therapeutically active compounds.

Where the compounds of the present invention are used as analgesics against diseases accompanied with pain such as cancerous pain, postoperative pain, migraine, gout, chronic rheumatism, chronic pain and neuralgia; relievers against tolerance to narcotic analgesic represented by morphine; relievers against dependence on narcotic analgesic represented by morphine or against addiction; analgesic enhancer; antiobestic or appetite suppressors; treating or prophylactic agents for cognitive impairment and dementia/amnesia in aging, cerebrovascular diseases and Alzheimer's disease; agents for treating developmental cognitive abnormality in attention deficit, hyperactivity disorder and learning disability; remedy for schizophrenia; agents for treating neurodegenerative diseases represented by Parkinsonism and chorea; anti-depressants or treating agents for affective disorder; treating or prophylactic agents for diabetes insipidus; treating or prophylactic agents for polyuria; or remedy for hypotension; their administration dosage or frequency can be varied depending on gender, age, body weight, degree of symptoms of individual patients and kind and extent of intended therapeutic effect. In general terms, the dose can normally range from 0.001 to 50 mg per day per kilogram of body weight, which can be administered at a time or by plural times. Preferably the dose is within a range of from about 0.01 to about 25 mg/kg per day, in particular, from about 0.05 to about 10 mg/kg per day.

EXAMPLES

Hereinafter the present invention is explained more specifically, referring to working Examples, it being understood that the invention is not limited to those working Examples. Unless otherwise specified, those various reagents used in the working Examples were those available on the market, and, H-NMR values were measured, using tetramethylsilane as the reference material, using AL-400-2 (400 MHz, JEOL Co). Also the mass spectra were measured with Micromass ZQ (Waters Co.), by electro spray ionizing method (ESI) or atmospheric pressure chemical ionization method (APCI).

Production Example 1

Production of spiro[4.5]decane-6-carbaldehyde

1) Spiro[4.5]decane-6-one

Cyclohexanone (3.0 mL) was dissolved in toluene (60 mL), and cooled to 0° C. in nitrogen atmosphere. Potassium tert-butoxide (6.86 g) was added to the reaction mixture at 0° C. and stirred for 30 minutes. To the resulting suspension, 1,4-dibromomethane (3.65 mL) was added, and then the reaction mixture was stirred at 150° C. for 6 hours. Cooling the reaction mixture to room temperature, water was added thereto, followed by extraction with ethyl acetate. The extract was dried over anhydrous magnesium sulfate, the solvent was removed by distillation, and the resulting residue was purified on silica gel column chromatography (hexane/ethyl acetate=50/1) to provide 690.0 mg of the title compound as a colorless, oily substance.

2) Spiro[4.5]decane-6-carbaldehyde

A solution of diethyl(isocyanomethyl)phosphonate (410 μL) in diethyl ether (5 mL) was cooled to −78° C. in nitrogen atmosphere. After addition of 1.54M n-butyl lithium solution in hexane (1.7 mL) to the reaction mixture at −78° C., the temperature was raised to 0° C. and stirred for 15 minutes. To the resulting solution spiro[4.5]decane-6-one (300 mg) was added at 0° C., and the temperature was raised to room temperature under stirring. An hour thereafter, conc. hydrochloric acid (5 mL) was added to the reaction mixture at room temperature, followed by further 10 hours' stirring. The resulting solution was diluted with water and extracted with diethyl ether. The extract was dried over anhydrous magnesium sulfate, and from which the solvent was distilled off to provide the title compound in crude, unpurified form, as a colorless oily substance.

Production Example 2

Preparation of spiro[3.5]nonane-5-carbaldehyde

1) Ethyl 1,4-dioxaspiro[4.5]decane-6-carboxylate

Ethyl 2-oxocyclohexane carboxylate (11.3 g) and ethylene glycol (11 mL) were dissolved in toluene (100 mL). To the reaction mixture camphorsulfonic acid (1.03 g) was added and refluxed for 8 hours with Dean-Stark apparatus. The reaction mixture was cooled to room temperature, diluted with diethyl ether and washed with saturated aqueous sodium hydrogencarbonate solution. The extract washed with saturated brine, dried over anhydrous magnesium sulfate, and from which the solvent was distilled off to provide a crude product of the title compound.

2) 1,4-Dioxaspiro[4.5]dec-6-ylmethanol

The compound as obtained in 1) was dissolved in tetrahydrofuran (120 mL) and cooled to 0° C. in nitrogen atmosphere. To the reaction mixture lithium aluminum hydride (3.06 g) was added at 0° C., and then the temperature was raised to room temperature, followed by an overnight stirring. The reaction mixture was again cooled to 0° C., to which sodium sulfate decahydrate was added and stirred for an hour, followed by drying by addition of anhydrous magnesium sulfate and filtering the insoluble matter off. Distilling off the solvent in the filtrate, 9.80 g of a crude product of the title compound was obtained.

3) 6-[(Benzyloxy)methyl]-1,4-dioxaspiro[4.5]decane

The compound (9.80 g) as obtained in 2) was dissolved in tetrahydrofuran (100 mL) and cooled to 0° C. in nitrogen atmosphere. To the reaction mixture 60-72% sodium hydride (in the form of an oil dispersion) (3.34 g) was added at 0° C., followed by 30 minutes' stirring. To the resulting reaction mixture, benzyl bromide (8.4 mL) was added at 0° C., the temperature was raised to room temperature, and the system was stirred for 3 hours. The reaction mixture was diluted with diethyl ether, and washed first with water and successively, with saturated brine. The organic layer was dried over anhydrous magnesium sulfate, the solvent was distilled off, and the resulting residue was purified on silica gel column chromatography (hexane/ethyl acetate=19/1) to provide 7.24 g of the title compound.

4) 2-[(Benzyloxy)methyl]cyclohexanone

The compound (3.37 g) as obtained in 3) was dissolved in tetrahydrofuran (30 mL), to which 10% hydrochloric acid (10 mL) was added at room temperature, followed by 3 hours' stirring. The reaction mixture was diluted with diethyl ether and washed first with water, successively with saturated aqueous sodium hydrogencarbonate solution and then with saturated brine. The organic layer was dried over anhydrous magnesium sulfate, the solvent was distilled off, and 2.94 g of a crude product of the title compound was obtained.

5) 2-[(Benzyloxy)methyl]-1-[1-(phenylthio)cyclopropyl]cyclohexanol

A cyclopropyl phenyl sulfide (2.33 mL) solution in tetrahydrofuran (50 mL) was cooled to 0° C. in nitrogen atmosphere. To the reaction mixture, 1.0 M n-butyl lithium hexane solution (16 mL) was added at 0° C., followed by an hour stirring. The reaction mixture was cooled to −78° C., and to which a tetrahydrofuran solution (10 mL) of the compound (2.94 g) as obtained in 4) was added at −78° C., followed by stirring at −78° C. for 30 minutes and then at 0° C. for an hour. Water was added to the reaction mixture which then was extracted with diethyl ether. The extract was washed first with water and then with saturated brine, dried over anhydrous magnesium sulfate, the solvent was removed by distillation, and the resulting residue was purified on silica gel column chromatography (hexane/ethyl acetate=19/1) to provide 3.04 g of the title compound.

6) 5-[(Benzyloxy)methyl]spiro[3.5]nonane-1-one

The compound (3.04 g) as obtained in 5) was dissolved in toluene (40 mL), to which p-toluenesulfonic acid monohydrate (1.60 g) and water (0.15 mL) were added and stirred at 90° C. for 5 hours. The reaction mixture was diluted with diethyl ether and washed with water, 10% aqueous sodium hydroxide solution and saturated brine, by the order stated. The organic layer was dried over anhydrous magnesium sulfate, the solvent was removed by distillation, and the resulting residue was purified on silica gel column chromatography (hexane/ethyl acetate=19/1) to provide 670 mg of the title compound.

7) 5-[(Benzyloxy)methyl]spiro[3.5]nonane

The compound (670 mg) as obtained in 6) was dissolved in diethylene glycol (3 mL), to which hydrazine monohydrate (1.5 mL) and potassium carbonate (838 mg) were added, followed by stirring under heating at 150° C. for 3 hours and at 200° C. for 5 hours. The reaction mixture was cooled to room temperature, diluted with diethyl ether, and then washed with 10% hydrochloric acid and then with saturated brine. The organic layer was dried over anhydrous magnesium sulfate and the solvent was removed by distillation, to provide 224 mg of a crude title compound.

8) Spiro[3.5]non-5-ylmethanol

The compound (224 mg) as obtained in 7) was dissolved in methanol (5 mL), to which a catalytic amount of activated carbon-carried palladium hydroxide was added, and the system was stirred at room temperature for 4 hours in hydrogen atmosphere of one atmospheric pressure. Filtering off the insoluble matter with Celite®, the filtrate was condensed to provide 151 mg of crude title compound.

9) Spiro[3.5]nonane-5-carbaldehyde

The compound (151 mg) as obtained in 8) was dissolved in dimethylsulfoxide (5 mL) and to which triethylamine (2 mL) and anhydrous sulfurylic acid-pyridine complex (1.17 g) were added, followed by an hour stirring at room temperature. The reaction mixture was diluted with diethyl ether and washed successively with water, 10% hydrochloric acid, saturated aqueous sodium hydrogen-carbonate solution and saturated brine. The organic layer was dried over anhydrous magnesium sulfate and the solvent was distilled off to provide 120 mg of crude title compound.

Production Example 3

Preparation of spiro[2.5]octane-4-carbaldehyde

1) Ethyl 1,4-dioxaspiro[4.5]dec-6-yl acetate

Ethyl (2-oxocyclohexyl)acetate (50.05 g) and ethylene glycol (45.5 mL) were dissolved in toluene (200 mL). p-Toluenesulfonic acid monohydrate (7.75 g) was added to the reaction mixture which then was refluxed for 5 hours using Dean-Stark apparatus. The reaction mixture was cooled to room temperature and saturated aqueous sodium hydrogencarbonate solution was added thereto, followed by extraction with ethyl acetate. The extract washed with saturated brine, dried over anhydrous magnesium sulfate and the solvent was removed by distillation to provide 76.54 g of crude title compound as a pale, yellowish brown oily substance.

2) 2-(1,4-Dioxaspiro[4.5]-dec-6-yl)ethanol

The compound (76.54 g) as obtained in 1) was dissolved in tetrahydrofuran (350 mL) and cooled to 0° C. in nitrogen atmosphere. To the reaction mixture lithium aluminum hydride (10.36 g) was added at 0° C., followed by 3 hours' stirring. To the resulting reaction liquid sodium sulfate decahydrate (51.85 g) was added and stirred at room temperature for an overnight. The insoluble matter in the solution was filtered off with Celite®, and the filtrate was condensed to provide crude title compound (63.77 g) as a pale yellow, oily substance.

3) 2-(2-Chloroethyl)cyclohexanone

The compound (63.77 g) as obtained in 2) was dissolved in acetonitrile (40 mL) and added to conc. hydrochloric acid (250 mL) which had been cooled to 0° C. The reaction mixture's temperature was raised to room temperature, followed by 1.5 hours' heating under reflux. The reaction mixture was cooled to room temperature, diluted with water and extracted with hexane. The extract was successively washed with water and then with saturated aqueous sodium hydrogencarbonate solution, dried over anhydrous sodium sulfate and the solvent was removed by distillation to provide crude title compound (46.15 g) as a pale yellow, oily substance.

4) Spiro[2.5]octane-4-one

The compound (46.15 g) as obtained in 3) was dissolved in ethanol (100 mL) and cooled to 0° C. To the reaction mixture powdery potassium hydroxide (19.97 g) was added at 0° C. and the temperature was raised to room temperature, followed by 3 hours' stirring. Potassium chloride as precipitated was filtered off, and the filtrate was used in the subsequent reaction as an ethanol solution of the title compound.

5) Spiro[2.5]octane-4-carbonitrile

Potassium tert-butoxide (158.0 g) was suspended in dimethylsulfoxide (370 mL), and into which p-toluenesulfonylmethyl isocyamide (60.60 g) was added under cooling with ice, followed by 15 minutes stirring at 0° C. Into the resulting brown-colored reaction mixture, an ethanol solution of the spiro[2.5]octane-4-one as obtained in 4) was added at 0° C., heated to room temperature and stirred for 3 hours. To the reaction mixture, water (300 mL) and hexane (300 mL) were added, followed by addition of 10% hydrochloric acid (400 mL). The reaction mixture was extracted with hexane, and the extract washed with water and saturated aqueous solution of sodium hydrogencarbonate. The organic layer was dried over anhydrous sodium sulfate, from which the solvent was distilled off, and the resulting residue was purified on silica gel column chromatography (hexane/ethyl acetate=3/1) to provide 39.95 g of the title compound as an yellowish brown, oily substance.

6) Spiro[2.5]octane-4-carbaldehyde

The compound (39.95 g) as obtained in 5) was dissolved in hexane (250 mL), and cooled to 0° C. in nitrogen atmosphere. To the reaction mixture, 0.95 M diisobutylaluminum hydride-in-hexane solution (400 mL) was dropped at 0° C. After the end of dropping, the reaction mixture was heated to room temperature and stirred for 3 hours. The

19 resulting reaction mixture was again cooled to 0° C. and into which 10% hydrochloric acid (300 mL) was dropped, followed by an hour stirring at room temperature. The reaction mixture was extracted with hexane, and to the hexane extract first water (1.5 L) and then sodium hydrogensulfite (500 g) were added, followed by vigorous stirring at room temperature to extract the title compound as its hydrogen sulfite adduct in a water layer. The aqueous layer as extracted was separated, and to which methyl tert-butyl ether (1 L) was added, followed by addition of sodium hydroxide (280 g) and vigorous stirring at room temperature. Separating the ether layer, the aqueous layer was again extracted with methyl tert-butyl ether. The resulting ether layers were combined and dried over anhydrous magnesium sulfate, and from which the solvent was distilled off to provide 20.04 g of the title compound as a pale yellow, oily substance.

Production Example 4

Preparation of spiro[bicyclo[2.2.1]heptane-2,1'-cyclopropane]-3-carbaldehyde

1) Spiro[bicyclo[2.2.1]heptane-2,1'-cyclopropane]-3-one

Zinc powder (15.10 g) was suspended in diethyl ether (70 mL) and to which cuprous chloride (2.29 g) was added at room temperature, followed by 30 minutes' refluxing in nitrogen atmosphere. The suspension was cooled to 0° C. and to which 3-methylenebicyclo[2.2.1]heptan-2-one (7.0 mL) was added at 0° C. Into the reaction mixture, methane diiodide (7.0 mL) was slowly dropped at 0° C. and after the end of the dropping, the reaction mixture was refluxed for 30 hours in nitrogen atmosphere. Cooling the reaction mixture to room temperature, the insoluble matter was filtered off with Celite® and the filtrate washed twice with 5% aqueous sodium thiosulfate solution. The organic layer was dried over anhydrous magnesium sulfate, the solvent was removed by distillation, and the resulting residue was purified on silica gel column chromatography (hexane/ethyl acetate=100/1–7/1) to provide 4.89 g of the title compound as a colorless oily substance.

2) Spiro[bicyclo[2.2.1]heptane-2,1'-cyclopropane]-3-carbaldehyde

Methoxymethyltriphenylphosphonium chloride (6.41 g) was suspended in tetrahydrofuran (80 mL) and cooled to 0° C. in nitrogen atmosphere. After adding 1.56 M n-butyl lithium-in-hexane solution (36.2 mL) at 0° C., the reaction mixture was stirred for an hour. Into the resulting deep red-colored solution, a spiro[bicyclo[2.2.1]heptane-2,1'-cyclopropane]-3-one (6.41 g) solution in tetrahydrofuran (10 mL) was dropped at 0° C., and thereafter the temperature was raised to room temperature, followed by an overnight's stirring. To the reaction mixture, 5M hydrochloric acid (50 mL) was added at room temperature and stirred for further 3 hours. The reaction mixture was diluted with water and extracted with diethyl ether. The extract washed with saturated brine, dried over anhydrous sodium sulfate, the solvent was removed by distillation and the resulting residue was purified on silica gel column chromatography (hexane/ethyl acetate=99/1–97/3) to provide 5.04 g of the title compound as a colorless oily substance.

20

Production Example 5

Preparation of (2,2-dimethyl-1,3-dioxolan-4-yl)methyl methanesulfonate 1) 2,2-Dimethyl-1,3-dioxolan-5-ol A 2,2-dimethyl-1,3-dioxolan-5-one (930 mg) solution in tetrahydrofuran (10 mL) was cooled to 0° C. in nitrogen atmosphere. To the reaction mixture lithium aluminium hydride (293 mg) was added at 0° C., followed by 30 minutes' stirring. After adding sodium sulfate decahydrate (3 g) to the reaction mixture at 0° C., the temperature was raised to room temperature, followed by further 2 hours' stirring. The insoluble matter was filtered off and the filterate was condensed. The resulting residue was purified on silica gel column chromatography (hexane/ethyl acetate=3/2) to provide 743 mg of the title compound as a colorless, oily substance.

2) 2,2-Dimethyl-1,3-dioxan-5-yl methanesulfonate

A 2,2-dimethyl-1,3-dioxolan-5-ol (743 mg) solution in tetrahydrofuran (10 mL) was cooled to 0° C. in nitrogen atmosphere. To the reaction mixture, triethylamine (1.87 mL) and methanesulfonyl chloride (520 μL) were successively added at 0° C., followed by 30 minutes' stirring. After addition of saturated aqueous ammonium chloride solution, the reaction mixture was extracted with ethyl acetate. The extract washed with saturated brine, dried over anhydrous magnesium sulfate and the solvent was removed by distillation to provide 837 mg of crude title compound as a colorless solid.

Production Example 6

Preparation of [(4R or 4S)-2,2,4-trimethyl-1,3-dioxolan-4-yl]methyl 4-methylbenzenesulfonate Two kinds of optical isomers of (2,2,4-trimethyl-1,3-dioxolan-4-yl)methyl 4-methylbenzenesulfonate (976 mg) which is a per se known substance, was separated using CHIRALPAK® AD (Daicel Co., Ltd., 2 cmϕ×25 cm; hexane/ethanol=9/1), to provide as the first eluate 478 mg of (4S or 4R) isomer of the title compound, and as the second eluate, 477 mg of (4R or 4S) isomer of the title compound.

Example 1

Preparation of 1-[(2R)-2,3-dihydroxypropyl]-3-{1-[(6S or 6R)-spiro[4.5]dec-6-ylmethyl]piperidin-4-yl}-1,3-dihydro-2H-benzimidazol-2-one 1) 3-[(1-(spiro[4.5]dec-6-ylmethyl)piperidin-4-yl)-1,3-dihydro-2H-benzimidazol-2-one To a 1-piperidin-4-yl-1,3-dihydro-2H-benzimidazol-2-one (360 mg) solution in dichloromethane (15 mL), the compound (250 mg) as obtained in Production Example 1 was added at room temperature, followed by addition of sodium triacetoxyborohydride (380 mg) at room temperature. The mixed solution was stirred at room temperature for 3 hours, 1M aqueous sodium hydroxide solution was added, and the reaction mixture was extracted with chloroform. The extract washed with saturated brine, dried over anhydrous magnesium sulfate, the solvent was removed by distillation, and the resulting residue was purified on silica gel column chromatography (chloroform/methanol=50/1–30/1) to provide 179.5 mg of the title compound as a colorless solid.

2) 1-{[(4R)-2,2-dimethyl-1,3-dioxolan-4-yl]methyl}-3-[1-(spiro[4.5]-dec-6-ylmethyl)piperidin-4-yl]-1,3-dihydro-2H-benzimidazol-2-one The compound (90 mg) as obtained in 1) was dissolved in dimethylformamide (3 mL), and to the solution 60-72% sodium hydride (oil dispersion) (20 mg) was added at room temperature, followed by 30 minutes' stirring. After addition of [(4S)-2,2-dimethyl-1,3-dioxolan-4-yl]methyl 4-methylbenzene-sulfonate (140 mg) and potassium iodide (20 mg), the reaction mixture was stirred at 60° C. for 14 hours. The reaction mixture was cooled to room temperature, to which 1M aqueous sodium hydroxide solution was added, followed by extraction with ethyl acetate. The extract washed with saturated brine, dried over anhydrous magnesium sulfate, the solvent was removed by distillation, and the resulting residue was purified on silica gel column chromatography (hexane/ethyl acetate=5/1–2/1) to provide 100.2 mg of the title compound as a pale yellow, oily substance.

3) 1-{[(4R)-2,2-dimethyl-1,3-dioxolan-4-yl]methyl}-3-{1-[(6S or 6R)-spiro[4.5]-dec-6-ylmethyl)piperidin-4-yl]-1,3-dihydro-2H-benzimidazol-2-one The two kinds of diastereomers of the compound (100.2 mg) as obtained in 2) were separated using CHIRALPAK® AD (Daicel Co., Ltd.; 2 cmϕ×25 cm, hexane/2-propanol/diethylamine=6/1/0.007), to provide as the first eluate 44.1 mg of (6S or 6R) isomer of the title compound.

4) 1-[(2R)-2,3-dihydroxypropyl]-3-{1-[(6S or 6R)-spiro[4.5]dec-6-ylmethyl]piperidin-4-yl}-1,3-dihydro-2H-benzimidazol-2-one The compound (44 mg) as obtained in 3) was dissolved in tetrahydrofuran (2 mL), to which 5M hydrochloric acid (2 mL) was added at room temperature and stirred for an hour. The resulting reaction solution was cooled to 0° C., neutralized with 1M aqueous sodium hydroxide solution and extracted with ethyl acetate. The extract washed with saturated brine, dried over anhydrous magnesium sulfate, the solvent was removed by distillation and the resulting residue was purified on silica gel preparative thin layer chromatography (chloroform/methanol=20/1) to provide 28.8 mg of the title compound as a colorless oily substance.

$^1$H-NMR(CDCl$_3$) δ=1.14-1.85(19H,m), 1.88-1.99(1H,m),
2.14-2.55(5H,m), 2.90-2.99(1H,m), 3.05-3.14(1H,m),
3.55-3.62(2H,m), 3.96-4.10(3H,m), 4.26-4.40(1H,m),
7.07-7.15(3H,m), 7.28-7.34(1H,m)
ESI-MS(+20 eV) m/z 442.2

Example 2

Preparation of 1-[(2R)-2,3-dihydroxypropyl]-3-{1-[(4S)-spiro[2.5]oct-4-ylmethyl]piperidin-4-yl}-1,3-dihydro-2H-benzimidazol-2-one 1) 3-[1-(spiro[2.5]oct-4-ylmethyl)piperidin-4-yl]-1,3-dihydro-2H-benzimidazol-2-one To 1-piperidin-4-yl-1,3-dihydro-2H-benzimidazol-2-one (4.00 g) solution in tetrahydrofuran (150 mL), the compound (3.02 g) as obtained in Production Example 3 was added at room temperature, and successively, sodium triacetoxyborohydride (4.68 g), at room temperature. The mixed solution was stirred at room temperature for 2 hours, followed by addition of 1.5M aqueous sodium hydroxide solution and extraction with chloroform. The extract was dried over anhydrous magnesium sulfate and the solvent was removed by distillation to provide 4.98 g of crude title compound as a pale, yellowish brown solid.

2) 1-(Methylsulfonyl)-3-[1-(spiro[2.5]oct-4-ylmethyl)piperidin-4-yl]-1,3-dihydro-2H-benzimidazol-2-one The compound (4.98 g) as obtained in 1) was dissolved in chloroform (150 mL). To the solution triethylamine (7 mL) and methanesulfonyl chloride (1.94 mL) were added at room temperature, followed by 2 hours' stirring at room temperature. The reaction mixture was diluted with chloroform and washed with saturated aqueous sodium hydrogencarbonate solution. The organic layer was dried over anhydrous magnesium sulfate, the solvent was removed by distillation and the resulting residue was purified on silica gel column chromatography (chloroform/methanol=100/1–15/1) to provide 5.47 g of the title compound as a pale yellow, oily substance.

3) 1-(Methylsulfonyl)-3-{1-[(4S)-spiro[2.5]oct-4-ylmethyl)piperidin-4-yl}-1,3-dihydro-2H-benzimidazol-2-one The two kinds of diastereomers of the compound (5.47 g) as obtained in 2) were separated using CHIRALPAK® AD (Daicel Co., Ltd.; 2 cmϕ×25 cm, hexane/ethanol/diethylamine=4/1/0.005) to provide as the first eluate 2.15 g of (4S) isomer of the title compound.

4) 3-{-[(4S)-spiro[2.5]oct-4-ylmethyl]piperidin-4-yl}-1,3-dihydro-2H-benzimidazol-2-one The compound (2.15 g) as obtained in 3) was dissolved in tetrahydrofuran (70 mL), to which 1M tetra-n-butylammonium fluoride-in-tetrahydrofuran solution (9.5 mL) was added at room temperature and stirred for 3 hours. Saturated aqueous sodium hydrogencarbonate solution was added to the reaction mixture which then was extracted with ethyl acetate. The extract washed with saturated brine, dried over anhydrous magnesium sulfate, the solvent was removed by distillation and the resulting residue was purified on basic silica gel column chromatography (hexane/ethyl acetate=1/1–1/2) to provide 1.56 g of the title compound as a colorless solid.

5) 1-{[(4R)-2,2-dimethyl-1,3-dioxolan-4-yl]methyl}-3-{1-[(4S)-spiro-[2.5]-oct-4-ylmethyl]piperidin-4-yl}-1,3-dihydro-2H-benzimidazol-2-one 3-{1-[(4S)-spiro[2.5]oct-4-ylmethyl]piperidin-4-yl}-1,3-dihydro-2H-benzimidazol-2-one (2.94 g) was dissolved in dimethylformamide (60 mL), and to which 60-72% sodium hydride (oil dispersion) (706.6 mg) was added at room temperature and stirred for 30 minutes. To the reaction mixture, [(4S)-2,2-dimethyl-1,3-dioxolan-4-yl]methyl 4-methylbenzene-sulfonate (7.25 g) was added and stirred at 80° C. for 7 hours. After cooling the reaction mixture to room temperature, water was added, followed by extraction with ethyl acetate. The extract washed with saturated brine, dried over anhydrous magnesium sulfate, the solvent was removed by distillation and the resulting residue was purified on silica gel column chromatography (hexane/ethyl acetate=2/1–1/2) to provide 3.43 g of the title compound as a pale yellow, oily substance.

6) 1-[(2R)-2,3-dihydroxypropyl]-3-{1-[(4S)-spiro[2.5]oct-4-ylmethyl]-piperidin-4-yl}-1,3-dihydro-2H-benzimidazol-2-one hydrochloride The compound (2.71 g) as obtained in 5) was dissolved in methanol (15 mL), to which 10% hydrogen chloride/methanol solution (65 mL) was added and stirred overnight at room temperature. The reaction mixture was condensed, and the resulting solid washed with ethanol to provide 1.60 g of the title compound as a colorless solid.
$^1$H-NMR(CDCl$_3$) δ=0.31-0.42(2H,m), 0.42-0.58(2H,m), 0.76-0.86(1H,m), 1.40-1.75(4H,m), 1.75-2.10(4H,m), 2.72-3.00(4H,m), 3.22-3.42(3H,m), 3.52-3.64(3H,m), 3.65-3.78(2H,m), 4.00-4.08(3H,m), 4.65-4.80(1H,m), 7.10-7.20(3H,m), 8.02-8.08(1H,m), 12.60(1H,brs)
ESI-MS(+20 eV) m/z 414.4

Example 3

Preparation of 1-[2-hydroxy-1-(hydroxymethyl)ethyl]-3-{1-[(1R,3S,4S)-spiro[bicyclo[2.2.1]heptane-2,1'-cyclopropan-3-ylmethyl]-piperidin-4-yl}-1,3-dihydro-2H-benzimidazol-2-one

1) 3-[1-(Spiro[bicyclo[2.2.1]heptane-2,1'-cyclopropan]-3-ylmethyl)-piperidin-4-yl]-1,3-dihydro-2H-benzimidazol-2-one To 1-piperidin-4-yl-1,3-dihydro-2H-benzimidazol-2-one (1.5 g) solution in tetrahydrofuran (15 mL), the compound (1.2 g) as obtained in Production Example 4 was added at room temperature, and successively sodium triacetoxyborohydride (2.0 g) was added and stirred for 2 days at room temperature. To the reaction mixture 1M aqueous sodium hydroxide solution was added, followed by extraction with ethyl acetate. The extract was dried over anhydrous magnesium sulfate, then the solvent was distilled off and the resulting residue was purified on silica gel column chromatography (chloroform/methanol=100/1–10/1) to provide 1.53 g of the title compound as a pale orange-colored solid.

2) 1-(Methylsulfonyl)-3-[1-(spiro[bicyclo[2.2.1]heptane-2,1'-cyclopropan]-3-ylmethyl)piperidin-4-yl]-1,3-dihydro-2H-benzimidazol-2-one The compound (1.53 g) as obtained in 1) was dissolved in chloroform (15 mL) and cooled to 0° C. To the solution first triethylamine (1.2 mL) and successively methanesulfonyl chloride (512 μL) were added at 0° C., followed by an hour stirring at 0° C. The reaction mixture was diluted with ethyl acetate and washed with 1M aqueous sodium hydroxide solution. The organic layer was dried over anhydrous magnesium sulfate and the solvent was removed by distillation. The resulting residue was purified on silica gel column chromatography (chloroform/methanol=200/1–20/1) to provide 1.90 g of the title compound as a pale yellow, oily substance.

3) 1-(Methylsulfonyl)-3-{1-[(1R,3S,4S)-spiro[bicyclo[2.2.1]heptane-2,1'-cyclopropan]-3-ylmethyl]piperidin-4-yl}-1,3-dihydro-2H-benzimidazol-2-one The four kinds of optical isomers of the compound (1.90 g) as obtained in 2) were separated using CHIRALPAK® AD (Daicel Co., Ltd.; 2 cmφ×25 cm, hexane/ethanol/diethylamine=9/1/0.01), to provide as the third eluate 420 mg of the title compound (1R,3S,4S) isomer.

4) 3-{1-[(1R,3S,4S)-spiro[bicyclo[2.2.1]heptane-2,1'-cyclopropan]-3-ylmethyl]piperidin-4-yl}-1,3-dihydro-2H-benzimidazol-2-one The third eluate (420 mg) as obtained in 3) was dissolved in tetrahydrofuran (5 mL), and to which 1M tetra-n-butylammonium fluoride solution in tetrahydrofuran (1.5 mL) was added at room temperature and stirred overnight. After distilling off the solvent from the reaction mixture, the resulting residue was purified on silica gel column chromatography (chloroform/methanol=100/1–10/1) to provide 294 mg of the title compound as a colorless solid.

5) 1-(2,2-Dimethyl-1,3-dioxolan-5-yl)-3-{1-[(1R,3S,4S)-spiro-[bicyclo[2.2.1]heptane-2,1'-cyclopropan]-3-ylmethyl]piperidin-4-yl}-1,3-dihydro-2H-benzimidazol-2-one The compound (294 mg) as obtained in 4) above was dissolved in dimethylformamide (5 mL), and to which 60-72% sodium hydride (an oil dispersion) (100 mg) was added at room temperature and stirred for 30 minutes. To the resulting reaction mixture the compound (353 mg) as obtained in Production Example 5 was added and stirred at 120° C. for 2 hours. Thereafter 60-72% sodium hydride (an oil dispersion) (100 mg) and the compound (353 mg) as obtained in Production Example 5 was added to the reaction mixture twice at an interval of an hour. The reaction mixture was cooled to room temperature, to which 1M aqueous sodium hydroxide solution was added and extracted with ethyl acetate. The extract washed with saturated brine, dried over anhydrous magnesium sulfate, the solvent was removed by distillation and the resulting residue was purified on silica gel column chromatography (chloroform/methanol=400/1–20/1) to provide 132 mg of the title compound as a pale yellow, oily substance.

6) 1-[2-hydroxy-1-(hydroxymethyl)ethyl]-3-{1-[(1R,3S,4S)-spiro-bicyclo[2.2.1]heptane-2,1'-cyclopropan]-3-ylmethyl]piperidin-4-yl}-1,3-dihydro-2H-benzimidazol-2-one hydrochloride The compound (132 mg) as obtained in 5) was dissolved in methanol (5 mL), to which 6M hydrochloric acid (100 μL) was added at room temperature and stirred for 3 hours.

Distilling the solvent off from the reaction mixture, the resulting solid washed with ethyl acetate to provide 128 mg of the title compound as a colorless solid.

$^1$H-NMR(CD$_3$OD) δ0.29-0.39(2H,m), 0.46-0.55(1H,m), 0.66-0.74(1H,m), 1.46-1.68(6H,m), 1.79-1.86(1H,m), 2.00-2.12(2H,m), 2.28-2.37(1H,m), 2.53-2.59(1H,m), 2.74-3.26(5H,m), 3.49-3.62(1H,m), 3.71-3.82(2H,m), 3.94(2H,dd,J=5.3,11.6 Hz), 4.08(2H,dd,J=8.1,11.6 Hz), 4.45-4.65(2H,m), 7.06-7.14(2H,m), 7.28-7.41(2H,m)
ESI-MS(+20 eV) m/z 426.2

Example 4

Preparation of 1-[(2S or 2R)-2,3-dihydroxy-2-methylpropyl]-3-{1-[(4S)-spiro[2.5]oct-4-ylmethyl]piperidin-4-yl}-1,3-dihydro-2H-benzimidazol-2-one (2R,3R)-3-carboxy-2,3-dihydroxypropionic acid salt 1) 1-{1-[(4S)-spiro[2.5]oct-4-ylmethyl]piperidin-4-yl}-3-{[(4S or 4R)-2,2,4-trimethyl-1,3-dioxolan-4-yl]methyl}-1,3-dihydro-2H-benzimidazol-2-one 3-{1-[(4S)-spiro[2.5]oct-4-ylmethyl]piperidin-4-yl}-1,3-dihydro-2H-benzimidazol-2-one (753 mg) as obtained in Example 2-4) and potassium iodide (372 mg) were dissolved in dimethylformamide (100 mL), and to which 60-72% sodium hydride (an oil dispersion) (428 mg) was added at room temperature and stirred for 30 minutes. To the resulting reaction mixture, a solution of the (4R or 4S)-2,2,4-trimethyl-1,3-dioxolan-4-yl]methyl 4-methylbenzenesulfonate (1.99 g), as obtained in Production Example 6 as the second eluate, in dimethylformamide (30 mL) was added at room temperature and stirred at 120° C. for an overnight. To the reaction mixture saturated aqueous ammonium chloride solution was added, followed by extraction with ethyl acetate. The extract washed with saturated aqueous sodium hydrogen-carbonate solution, dried over anhydrous magnesium sulfate, the solvent was removed by distillation and the resulting residue was purified on basic silica gel column chromatography (hexane/ethyl acetate=10/1–5/1) to provide 1.27 g of the title compound as a pale yellow, oily substance.

2) 1-[(2S or 2R)-2,3-dihydroxy-2-methylpropyl]-3-{1-[(4S)-spiro-[2.5]oct-4-ylmethyl]piperidin-4-yl}-1,3-dihydro-2H-benzimidazol-2-one.(2R,3R)-3-carboxy-2,3-dihydroxypropionic acid salt The compound (1.27 g) as obtained in 1) was dissolved in tetrahydrofuran (20 mL), and to which 1M hydrochloric acid (20 mL) was added at room temperature and stirred overnight. The resulting reaction mixture was cooled to 0° C., and to which saturated aqueous sodium hydrogencarbonate solution was added, followed by extraction with chloroform. The extract was dried over anhydrous magnesium sulfate, the solvent was removed by distillation and the resulting residue was purified on silica gel column chromatography (chloroform/methanol=30/1–4/1) to provide 1.09 g of free amine of the title compound. This free amine (33.2 mg) and (2R,3R)-tartaric acid (11.6 mg) were dissolved in methanol (3 mL), and the solvent was distilled off. The resulting solid washed with ethyl acetate to provide 44.8 mg of the title compound as a colorless solid.

$^1$H-NMR(CD$_3$OD) δ=0.35(2H,brs), 0.45(2H,brs), 0.84(1H,m),
1.14(1H,d,J=6.2 Hz), 1.20(3H,s), 1.41-1.82(8H,m),2.01(2H,m), 2.78-3.25(5H,m), 3.30-3.51 (2H,m), 3.69(2H,m), 3.92(2H,s),
4.43(2H,s), 4.60(1H,m), 7.12(2H,m), 7.36(2H,m)
ESI-MS(+20 eV) m/z 428.3

Example 5

Preparation of 1-[(2R)-2,3-dihydroxypropyl]-3-{1-[(1R,3S,4S)-spiro[bicyclo-[2.2.1]heptane-2,1'-cyclopropan]-3-ylmethyl]piperidin-4-yl}-1,3-dihydro-2H-benzimidazol-2-one hydrochloride 1) 1-{[(4R)-2,2-dimethyl-1,3-dioxolan-4-yl]methyl}-3-{1-[(1R,3S,4S)-spiro[bicyclo[2.2.1]heptane-2,1'-cyclopropan]-3-ylmethyl]piperidin-4-yl}-1,3-dihydro-2H-benzimidazol-2-one 3-{1-[(1R,3S,4S)-spiro[bicyclo[2.2.1]heptane-2,1'-cyclopropan]-3-ylmethyl]piperidin-4-yl}-1,3-dihydro-2H-benzimidazol-2-one (1.47 g) as obtained in 4) of Example 3 was dissolved in dimethylformamide (25 mL), and to which 60-72% sodium hydride (an oil dispersion) (418 mg) was added at room temperature and stirred for 15 minutes. To the resulting reaction mixture, a [(4S)-2,2-dimethyl-1,3-dioxolan-4-yl]methyl 4-methylbenzenesulfonate (2.39 g) solution in dimethylformamide (5 mL) was added at room temperature, and stirred at 80° C. for 5 hours. The reaction mixture was cooled to room temperature, to which phosphate buffer (pH 6.5) was added, followed by extraction with ethyl acetate. The extract washed with water, dried over anhydrous sodium sulfate, the solvent was removed by distillation and the resulting residue was purified on silica gel column chromatography (hexane/ethyl acetate=9/1–1/1) to provide 1.80 g of the title compound as a colorless, oily substance.

2) 1-[(2R)-2,3-dihydroxypropyl]-3-{1-[(1R,3S,4S)-spiro[bicyclo[2.2.1]heptane-2,1'-cyclopropan]-3-ylmethyl]piperidin-4-yl}-1,3-dihyro-2H-benzimidazol-2-one hydrochloride The compound (1.75 g) as obtained in 1) was dissolved in tetrahydrofuran (57 mL), to which 1M hydrochloric acid (19 mL) was added at room temperature and stirred for 30 hours. The reaction mixture was neutralized by addition of aqueous sodium hydrogencarbonate solution at 0° C., followed by extraction with ethyl acetate. The extract washed with saturated brine, dried over anhydrous sodium sulfate, the solvent was removed by distillation and the resulting residue was purified on silica gel column chromatography (chloroform/methanol=1/0–95/5) to provide 1.42 g of free amine of the title compound. The amine was dissolved in diethyl ether, to which 4M hydrogen chloride solution in dioxane (0.92 mL) was added at room temperature. Distilling the solvent off from the resulting suspension, the remaining solid washed with ethanol/ethyl acetate (1/1) mixture to provide 1.06 g of the title compound as a colorless solid.

$^1$H-NMR(CD$_3$OD) δ=0.27-0.38(2H,m), 0.43-0.57(1H, m),
0.63-0.73(1H,m), 1.40-1.69(6H,m), 1.78-1.87(1H,m), 1.96-2.09(2H,m), 2.27-2.37(1H,m), 2.52-2.60(1H,m), 2.70-3.27(6H,m), 3.51-3.60(2H,m), 3.65-3.80(2H,m), 3.87-4.03(3H,m), 4.52-4.67(1H,m), 7.08-7.16(2H,m), 7.22-7.29(1H,m), 7.32-7.41(1H,m)
ESI-MS(+20 eV) m/z 426.2

INDUSTRIAL APPLICABILITY

The compounds of the invention have the action to inhibit binding of nociceptin to nociceptin receptor ORL1 and are useful as analgesics against diseases accompanied with pain such as cancerous pain, postoperative pain, migraine, gout, chronic rheumatism, chronic pain and neuralgia; relievers against tolerance to narcotic analgesic represented by morphine; relievers against dependence on narcotic analgesic represented by morphine or against addiction; analgesic enhancers; antiobestic or appetite suppressors; treating or prophylactic agents for cognitive impairment and dementia/amnesia in aging, cerebrovascular diseases and Alzheimer's disease; agents for treating developmental cognitive abnormality in attention deficit, hyperactivity disorder and learning disability; remedy for schizophrenia; agents for treating neurodegenerative diseases represented by Parkinsonism and chorea; anti-depressant or treating agents for affective disorder; treating or prophylactic agents for diabetes insipidus; treating or prophylactic agents for polyuria; and remedy for hypotension and the like.

The invention claimed is:

1. A compound of the formula (I):

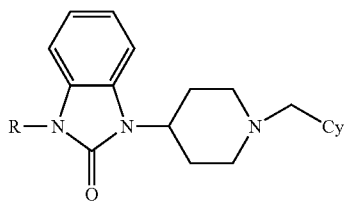

wherein:

R is a di-hydroxy-substituted $C_3$-$C_4$ alkyl group, and

Cy is selected from the group consisting of: spiro[4.5]dec-6-yl; spiro[2.5]oct-4-yl; spiro[3.5]non-5-yl; bicyclo[2.2.1]hept-2-yl; and 1-spiro(bicyclo[2.2.1]heptane-2,1'-cyclopropan)-3-yl, which is unsubstituted or substituted with a substituent selected from: halogen and $C_1$-$C_6$ alkyl;

or a pharmaceutically acceptable salt thereof.

2. The compound of claim 1, wherein R is selected from the group consisting of: 2-hydroxy-1-(hydroxymethyl)ethyl; 2,3-dihydroxypropyl; 2,3-dihydroxy-2-methylpropyl; 2,3-dihydroxybutyl; 2,4-dihydroxybutyl; 3,4-dihydroxybutyl; 2,3-dihydroxy-1-methylpropyl; 2-hydroxy-1-(hydroxymethyl)propyl; 3-hydroxy-1-(hydroxymethyl)propyl; and 3-hydroxy-2-(hydroxymethyl)propyl.

3. The compound of claim 2, wherein R is selected from the group consisting of: 2,3-dihydroxypropyl; 2-hydroxy-1-(hydroxymethyl)ethyl; and 2,3-dihydroxy-2-methylpropyl.

4. The compound of claim 1 wherein Cy is selected from the group consisting of: spiro[4.5]dec-6-yl; spiro[2.5]oct-4-yl; spiro[3.5]non-5-yl; 3,3-dimethylbicyclo[2.2.1]hept-2-yl; and 1-spiro(bicyclo[2.2.1]heptane-2,1'-cyclopropan)-3-yl.

5. The compound of claim 1 wherein Cy is unsubstituted.

6. The compound of claim 1 wherein Cy is substituted with a $C_1$-$C_4$ alkyl group.

7. A compound which is selected from the group consisting of:

1-(2,3-dihydroxypropyl)-3-[1-(spiro[4.5]dec-6-ylmethyl)-piperidin-4-yl]-1,3-dihydro-2H-benzimidazol-2-one;

1-(2,3-dihydroxypropyl)-3-[1-(spiro[2.5]oct-4-ylmethyl)-piperidin-4-yl]-1,3-dihydro-2H-benzimidazol-2-one;

1-[2-hydroxy-1-(hydroxymethyl)ethyl]-3-[1-(spiro[bicyclo-[2.2.1]heptane-2,1'-cyclopropan]-3-ylmethyl)piperidin-4-yl]-1,3-dihydro-2H-benzimidazol-2-one;

1-(2,3-dihydroxy-2-methylpropyl)-3-[1-(spiro[2.5]oct-4-ylmethyl)piperidin-4-yl]-1,3-dihydro-2H-benzimidazol-2-one; and 1-(2,3-dihydroxypropyl)-3-[1-(spiro[bicyclo[2.2.1]heptane-2,1'-cyclopropan]3-ylmethyl)piperidin-4-yl]-1,3-dihydro-2H-benzimidazol-2-one, or a pharmaceutically acceptable salt thereof.

8. The compound of claim 7 which is 1-[(2R)-2,3-dihydroxypropyl]-3-{1-[(spiro[4.5]dec-6-ylmethyl)piperidin-4-yl}-1,3-dihydro-2H-benzimidazol-2-one, or a pharmaceutically acceptable salt thereof.

9. The compound of claim 7 which is 1-[(2R)-2,3-dihydroxypropyl]-3-{1-[(4S)-spiro[2.5]oct-4-ylmethyl]piperidin-4-yl}-1,3-dihydro-2H-benzimidazol-2-one, or a pharmaceutically acceptable salt thereof.

10. The compound of claim 7 which is 1-[2-hydroxy-1-(hydroxymethyl)-ethyl]-3-{1-[(1R,3S,4S)-spiro[bicyclo[2.2.1]heptane-2,1'-cyclopropan-3-ylmethyl]-piperidin-4-yl}-1,3-dihydro-2H-benzimidazol-2-one, or a pharmaceutically acceptable salt thereof.

11. The compound of claim 10 which is 1-[2-hydroxy-1-(hydroxymethyl)ethyl]-3-{1-[(1R,3S,4S)-spiro[bicyclo[2.2.1]heptane-2,1'-cyclopropan-3-ylmethyl]-piperidin-4-yl}-1,3-dihydro-2H-benzimidazol-2-one hydrochloride.

12. The compound of claim 7 which is 1-[2,3-dihydroxy-2-methylpropyl]-3-{1-[(4S)-spiro[2.5]oct-4-ylmethyl]piperidin-4-yl}-1,3-dihydro-2H-benzimidzol-2-one, or a pharmaceutically acceptable salt thereof.

13. The compound of claim 7 which is 1-[(2R)-2,3-dihydroxypropyl]-3-{1-[(1R,3S,4S)-spiro[bicyclo-[2.2.1]heptane-2,1'-cyclopropan]-3-ylmethyl]piperidin-4-yl}-1,3-dihydro-2H-benzimidazol-2-one, or a pharmaceutically acceptable salt thereof.

14. The compound of claim 13 which is 1-[(2R)-2,3-dihydroxy-propyl]-3-{1-[(1R,3S,4S)-spiro[bicyclo-[2.2.1]heptane-2,1'-cyclopropan]-3-ylmethyl]-piperidin-4-yl}-1,3-dihydro-2H-benzimidazol-2-one hydrochloride.

15. A pharmaceutical composition comprising a pharmaceutically acceptable adjuvant and the compound of claim 1 or a pharmaceutically acceptable salt thereof.

16. A pharmaceutical composition comprising a pharmaceutically acceptable adjuvant and the compound of claim 7 or a pharmaceutically acceptable salt thereof.

17. A pharmaceutical composition comprising a pharmaceutically acceptable adjuvant and the compound of claim 8 or a pharmaceutically acceptable salt thereof.

18. A pharmaceutical composition comprising a pharmaceutically acceptable adjuvant and the compound of claim 9 or a pharmaceutically acceptable salt thereof.

19. A pharmaceutical composition comprising a pharmaceutically acceptable adjuvant and the compound of claim 10 or a pharmaceutically acceptable salt thereof.

20. A pharmaceutical composition comprising a pharmaceutically acceptable adjuvant and the compound of claim 11 or a pharmaceutically acceptable salt thereof.

21. A pharmaceutical composition comprising a pharmaceutically acceptable adjuvant and the compound of claim 12 or a pharmaceutically acceptable salt thereof.

22. A pharmaceutical composition comprising a pharmaceutically acceptable adjuvant and the compound of claim 13 or a pharmaceutically acceptable salt thereof.

23. A pharmaceutical composition comprising a pharmaceutically acceptable adjuvant and the compound of claim 14 or a pharmaceutically acceptable salt thereof.

* * * * *